US007290543B2

(12) United States Patent
Stradella

(10) Patent No.: US 7,290,543 B2
(45) Date of Patent: Nov. 6, 2007

(54) FLUID PRODUCT DISPENSING DEVICE

(75) Inventor: Giuseppe Stradella, Camogli-Italie (IT)

(73) Assignee: Valois S.A.S., Neubourg (FR)

( * ) Notice: Subject to any disclaimer, the term of this patent is extended or adjusted under 35 U.S.C. 154(b) by 561 days.

(21) Appl. No.: 10/433,057

(22) PCT Filed: Nov. 30, 2001

(86) PCT No.: PCT/FR01/03801

§ 371 (c)(1),
(2), (4) Date: Dec. 8, 2003

(87) PCT Pub. No.: WO02/44056

PCT Pub. Date: Jun. 6, 2002

(65) Prior Publication Data

US 2005/0098175 A1 May 12, 2005

(30) Foreign Application Priority Data

Nov. 30, 2000 (FR) .................................. 00 15613

(51) Int. Cl.
*A61M 11/00* (2006.01)
*A61M 15/08* (2006.01)

(52) U.S. Cl. .......................... 128/200.22; 128/200.19; 128/203.22; 128/207.18

(58) Field of Classification Search ........... 128/200.14, 128/200.18, 200.19, 200.21, 200.22, 200.23, 128/202.17, 200.24, 203.22, 203.23, 203.25, 128/203.15, 203.21, 207.18, 913; 222/386, 222/378, 321.1, 321.6, 321.7, 321.8, 381, 222/391, 327, 326, 160, 162, 163; 604/151, 604/207, 211, 131, 209, 232, 208; 239/310, 239/322, 338, 350, 337, 586
See application file for complete search history.

(56) References Cited

U.S. PATENT DOCUMENTS 3,782,380 A * 1/1974 Van Der Gaast ............. 604/68
(Continued)

FOREIGN PATENT DOCUMENTS

FR 2 813 592 A1 3/2002

*Primary Examiner*—Justine R. Yu
*Assistant Examiner*—Annette Dixon
(74) *Attorney, Agent, or Firm*—Sughrue Mion, PLLC

(57) ABSTRACT

A fluid dispenser device having a body (1), a fluid reservoir (3) containing two half-doses, a dispensing mechanism that dispenses a half-dose of fluid upon actuation, and an energy accumulation mechanism (50, 51, 55) that accumulates energy in the hand of the user and released suddenly so that each of the half-doses is dispensed in full. The dispensing mechanism includes a dispensing member (8) mounted to slide in the reservoir (3) for dispensing the fluid, an actuating element (5) mounted to move between a rest position and an actuating position and on which the user exerts an actuating force to move the dispensing member (8) inside said reservoir (3). The actuating element is mounted to move in a direction substantially transverse to the direction in which the dispensing member (8) moves, and a dose-splitting mechanism (7, 12) dispenses a half-dose of fluid each time the dispensing mechanism is actuated.

9 Claims, 4 Drawing Sheets

U.S. PATENT DOCUMENTS

| | | | | | |
|---|---|---|---|---|---|
| 4,167,245 | A | | 9/1979 | Kock et al. | |
| 4,323,176 | A | * | 4/1982 | Sartain | 222/326 |
| 4,581,022 | A | * | 4/1986 | Leonard et al. | 604/229 |
| 4,678,106 | A | * | 7/1987 | Newell et al. | 222/162 |
| 4,860,738 | A | * | 8/1989 | Hegemann et al. | 128/200.22 |
| 4,962,868 | A | * | 10/1990 | Borchard | 222/49 |
| 5,289,818 | A | * | 3/1994 | Citterio et al. | 128/200.14 |
| 5,320,259 | A | * | 6/1994 | Weinstein | 222/391 |
| 5,431,155 | A | * | 7/1995 | Marelli | 128/200.14 |
| 5,501,373 | A | * | 3/1996 | Galli | 222/386 |
| 5,570,821 | A | | 11/1996 | DeJonge | |
| 5,899,365 | A | * | 5/1999 | Eichler et al. | 222/162 |
| 6,257,457 | B1 | * | 7/2001 | Oechsel | 222/320 |
| 6,296,484 | B1 | * | 10/2001 | Nihei et al. | 433/89 |
| 6,302,101 | B1 | * | 10/2001 | Py | 128/200.22 |
| 6,345,737 | B1 | * | 2/2002 | Martin et al. | 222/320 |
| 7,011,234 | B2 | * | 3/2006 | Stradella | 222/129 |
| 2004/0000306 | A1 | | 1/2004 | Stradella | |

* cited by examiner

FLUID PRODUCT DISPENSING DEVICE

FIELD OF THE INVENTION

The present invention relates to a fluid dispenser device, and more particularly to a device of the two-dose type, i.e. having two half-doses to be dispensed in succession.

BACKGROUND OF THE INVENTION

Dispenser devices of the two-dose type are well known. They are applicable particularly in dispensing medication and in particular vaccines into the nose. In existing devices, in order to subdivide the dose into two half-doses, e.g. so as to dispense them separately into respective ones of the two nostrils, two elements are generally provided, one supporting a reservoir, and the other supporting the piston. When they are compressed axially towards each other, the first half-dose is delivered through the dispensing orifice into the nostril. In order to subdivide the dose, the piston is stopped half way along its stroke by a shoulder, and, in order to cause it to travel over the second half of its stroke, i.e. in order to dispense the second half-dose, it is necessary to turn the piston element manually relative to the reservoir. That type of system is safe and accurate, but it requires relatively complex manipulation and therefore both hands to be used to obtain the desired result, and to make it possible to dispense the two half-doses successively into respective ones of the two nostrils. Unfortunately, the use of two hands for dispensing the two half-doses successively into respective ones of the two nostrils may be undesirable in certain cases, and in particular, it can be necessary to have one hand free for holding the head of a child to whom the fluid is being administered, for example.

In order to guarantee that each half-dose is dispensed in full, and in particular, in order to avoid partial dispensing and in order to achieve finely-sprayed dispensing, it is possible to provide energy accumulation means, such means generally having breakable bridges of material. Unfortunately, such a type of energy accumulation means, which is known from the state of the art, is unreliable because the bridges of material can break while the device is in transit, i.e. before it is used. Similarly, they do not make it possible to guarantee reliable and constant energy accumulation, it being possible for the breaking thresholds of said breakable bridges to vary due to various parameters, and in particular due to manufacturing tolerances. In addition, it is difficult to predetermine the force required to break said bridges of material, and thus the actuating force necessary for actuating the device.

SUMMARY OF THE INVENTION

An object of the present invention is to provide a fluid dispenser device, in particular of the two-dose type, that does not suffer from the above-mentioned drawbacks.

In particular, an object of the present invention is to provide a fluid dispenser device of the two-dose type that is simple and reliable to use, and that guarantees finely sprayed dispensing of an entire respective half-dose each time the device is actuated.

Another object of the present invention is to provide a fluid dispenser device of the two-dose type that does not involve any manipulation between the times the half-doses are dispensed, merely by actuating said device twice in succession.

A further object of the present invention is to provide such a fluid dispenser device of the two-dose type, in which the force necessary to actuate the device is easy to predetermine.

The present invention thus provides a fluid dispenser device comprising a body, a fluid reservoir containing two half-doses of fluid, a dispensing orifice, and dispensing means for dispensing a respective half-dose of fluid each time the dispensing means are actuated, said dispensing means being implemented so that each of the half-doses of fluid can be dispensed during a respective one of two successive occasions on which the dispensing means are actuated, it being possible to actuate the dispensing means on said successive occasions by the user of the device using a single hand, the dispenser device further comprising energy accumulation means adapted to accumulate energy in the hand of the user, said energy being released suddenly from a predetermined force exerted by the hand of the user on said dispensing means, thereby guaranteeing that each of the half-doses is dispensed in full, said fluid dispenser device being characterized in that the dispensing means comprise: a dispensing member, such as a piston, mounted to slide in said reservoir for dispensing the fluid; an actuating element mounted to move between a rest position and an actuating position, and on which the user exerts an actuating force to move said dispensing member inside said reservoir, said actuating element being mounted to move in a direction substantially transverse to the direction in which the dispensing member moves; and dose-splitting means for dispensing a half-dose of fluid each time the dispensing means are actuated.

Advantageously, the dose-splitting means are secured to said dispensing member, and are formed by a first projection co-operating with the actuating element when the device is actuated for the first time to dispense the first half-dose of fluid, and a second projection adapted to move out of the way while the first half-dose of fluid is being dispensed, said second pair of projections co-operating with said actuating element after the first half-dose has been dispensed, so as to dispense the second half-dose when the device is actuated for the second time.

Advantageously, said dose-splitting means co-operate with said actuating element to return it to its rest position after the first half-dose has been dispensed.

Advantageously, said actuating element has a cam surface co-operating with said dispensing member, preferably via said dose-splitting means.

Preferably, said energy accumulation means are exempt from breakable bridges of material.

Advantageously, said energy accumulation means comprise an elastically deformable element which deforms when it is subjected to said predetermined force.

Advantageously, said energy accumulation means comprise an elastically deformable catch provided on one of two elements that move relative to each other while the device is being actuated, said elastically deformable catch co-operating with the other of said two elements that move relative to each other to prevent them from moving relative to each other until a predetermined force is applied that is adapted to deform said elastically deformable catch.

In a first variant embodiment, said energy accumulation means are provided between said actuating element and said body of the device.

In a second variant embodiment, said energy accumulation means are provided between said dispensing member and the body of the device.

In a third variant embodiment, said energy accumulation means are provided between said actuating element and said dispensing member.

BRIEF DESCRIPTION OF THE DRAWINGS

Other characteristics and advantages of the present invention appear more clearly from the following detailed description of a particular embodiment of it given with reference to the accompanying figures which are given by way of non-limiting example, and which shows a diagrammatic views of an advantageous embodiment of a fluid dispenser device of the present invention and in which.

DETAILED DESCRIPTION OF EXEMPLARY EMBODIMENTS

Figure 1:
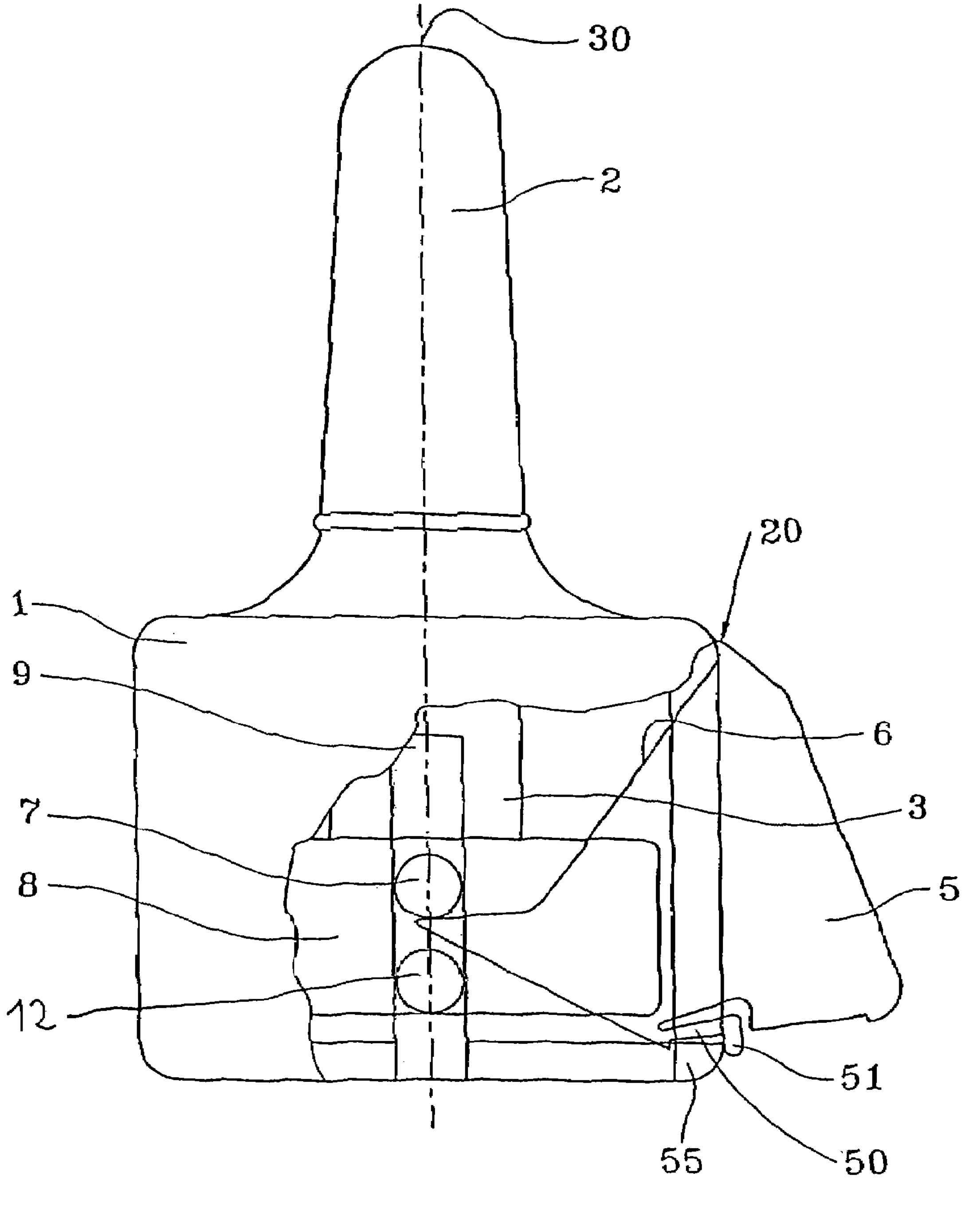
FIG. 1 is a view of a fluid dispenser in a rest position before a first half dose.

The present invention applies to any type of fluid dispenser of the two-dose type, but it is described below with reference more particularly to a device of the type disclosed in French patent application No. 00 11425, filed on Sep. 7, 2000. That patent application is therefore incorporated herein by way of reference, in particular as regards the general operation of the device, and more particularly of its actuating means and of its dose-splitting means.

French Application No. 00 114425 discloses a device that comprises a main body which supports a nasal applicator incorporating a dispensing orifice. A reservoir unit comprising a reservoir containing one dose or two half-doses of fluid is fixed into the body. The body is further provided with a hollow side sleeve which slidably receives an actuating element such as a push button. The actuating element is provided with a cam surface, which is preferably implemented in the form of one or more sloping surfaces. A dispensing member, such as a piston, is slidably mounted inside the reservoir, and it moves between a rest position and a delivery position, the piston moving axially inside said reservoir. Advantageously, the cam surface of the actuating element (in particular made up of the sloping surfaces) co-operates with at least one and preferably two projections which are formed on the piston element. The pair of projections are inserted into and slidably received in respective ones of two grooves which are formed in the wall of the cavity of the body in which the piston slides while it is being actuated. The actuating element may also be provided with retaining means which prevent the actuating element from being removed accidentally from the body, and with resilient return means which are not shown in the drawings. In an embodiment for a two-dose device, the piston is also provided with a second pair of projections, which are advantageously formed on two resilient arms which are integral parts of the piston. The projections are advantageously provided with thickened portions going towards the top portion of the device.

The device operates as follows. In order to dispense a first half-dose, the actuating element is pushed in a direction that is substantially perpendicular to the axial direction, and the sloping surfaces co-operate with the pair of projections to urge the piston axially, thereby causing it to slide upwards and to deliver the fluid. During this action, the second pair of projections reach the bottom face of the actuating element, at the cam surface, and, by means of the thickened potions and of the flexible arms, the projections slide under the actuating element until they reach the position, which corresponds to the end of dispensing of the first half-dose. Whereupon, when the actuating element ceases to be pressed, it returns to its rest position by means of resilient return means. While this is taking place, the second pair of projections are released, and the resilient arms can return, by their resilience, to their initial positions in which the projections are situated in the same positions as the pair of projections prior to delivery of the first half-dose. The device is then ready to dispense the second half-dose, which is achieved by pressing radially again on the actuating element. The advantage of the device is clear, namely that it is not necessary to turn the actuating element at all between delivery of the two half-doses. Therefore, the two half-doses can be dispensed successively into respective ones of the two nostrils by using one hand only.

However, the device disclosed in French Application No. 00 114425 is not limited to a device of the two-dose type, and it is also applicable to devices of the one-dose type, in which a single dose is to be delivered. In which case, the device operates similarly to the mode of operation described above, except that only one pair of projections is provided on the piston, since the projections and the arms are then unnecessary, as are the resilient return means.

In a second embodiment, the actuating element is not mounted to slide inside the body, but rather it is mounted to pivot on said body. The device operates relatively similarly to the mode of operation described above, the shape of the cam surface naturally being adapted to match the turning movement effected by the actuating element.

A device of the two-dose type operates similarly to the above described mode of operation, i.e., a second pair projections are provided on the piston, the projections moving out of the way when the actuating element is actuated to deliver the first half-dose, and then returning to the position corresponding to the first projections being in the initial position, for delivering the second half-dose.

Advantageously, the actuating element is made integrally with the body, and is connected thereto by a bridge of material which forms the pivot pin.

Advantageously, energy accumulation means may be provided on the actuating element or on the body, e.g., in the form of a lug or the like. The angle of inclination of the sloping surface may also be determined such as to increase the force exerted by the actuating element on piston or the reservoir.

In a variant to the above-described embodiments, the lateral actuating element may also co-operate with the reservoir unit. In which case, said reservoir unit incorporates the first and/or second projections. It is then the piston that is fixed relative to the body of the device, and the reservoir that is moved axially by the lateral actuating element.

However, it is clear that the present invention is not limited to this application, but rather, it can be used in any type of two-dose device.

Figure 2:
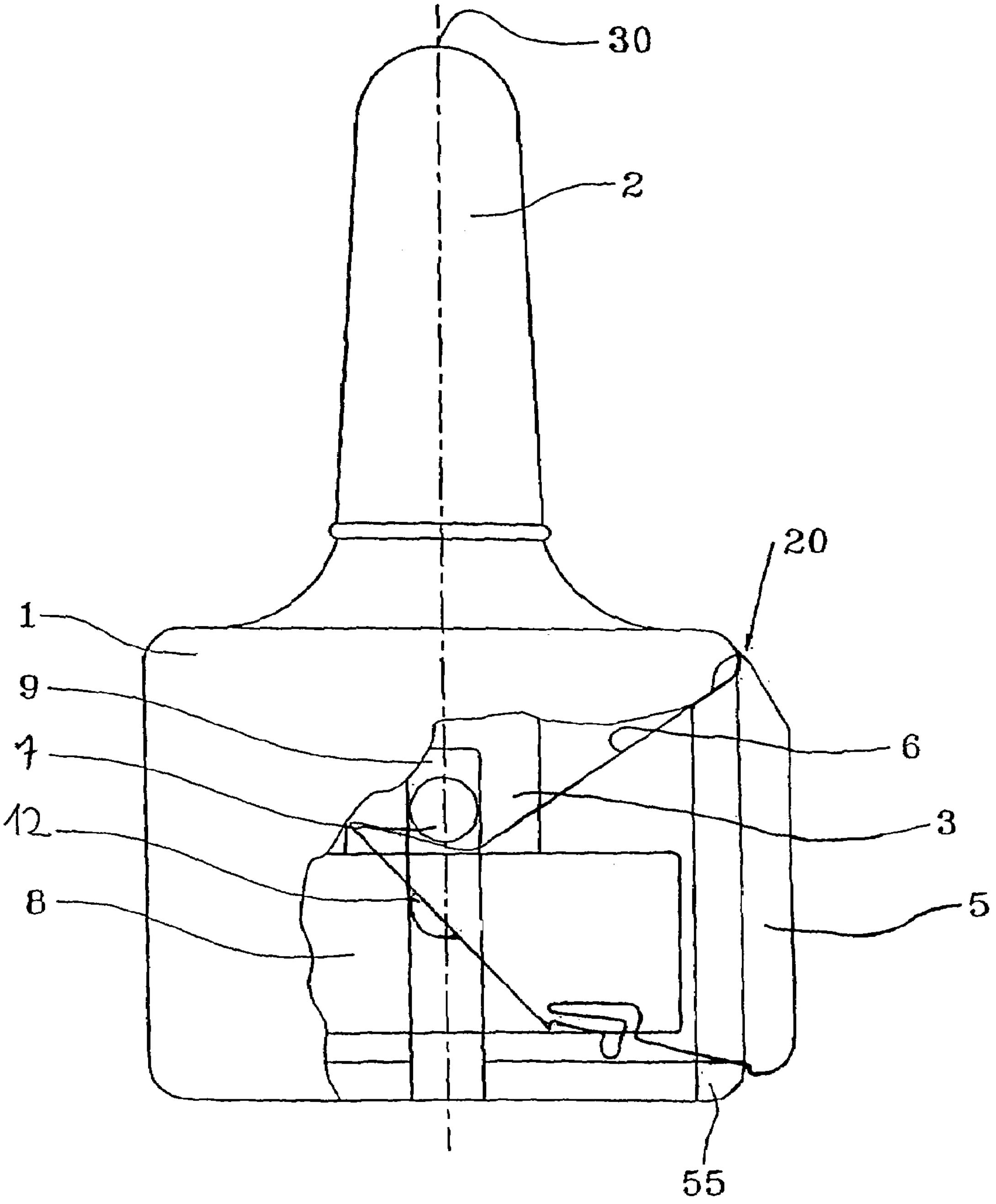
FIG. 2 is a view of the fluid dispenser in an actuating position for the first half dose.
Figure 3:
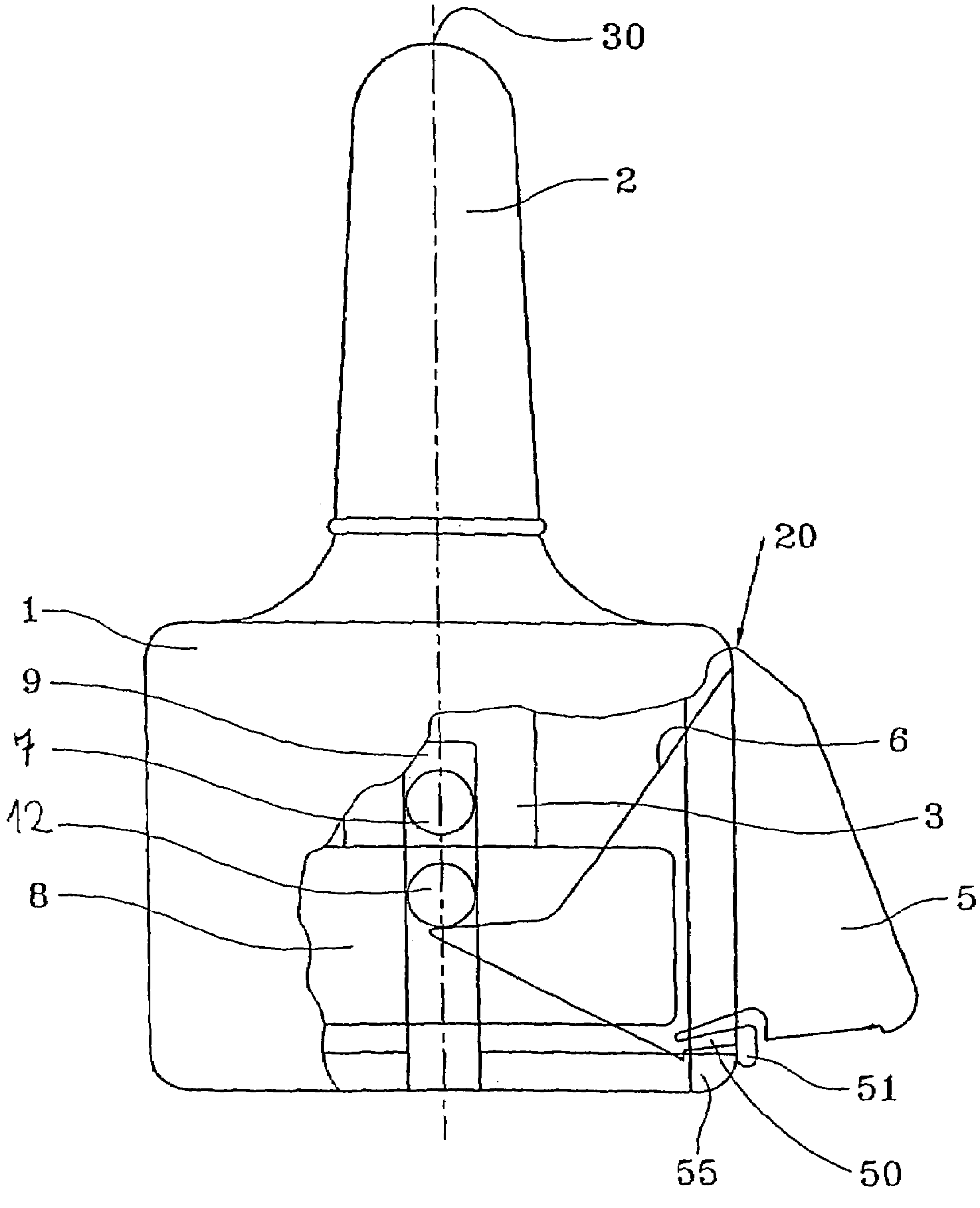
FIG. 3 is a view of the fluid dispenser in a rest position before a second half dose.
Figure 4:
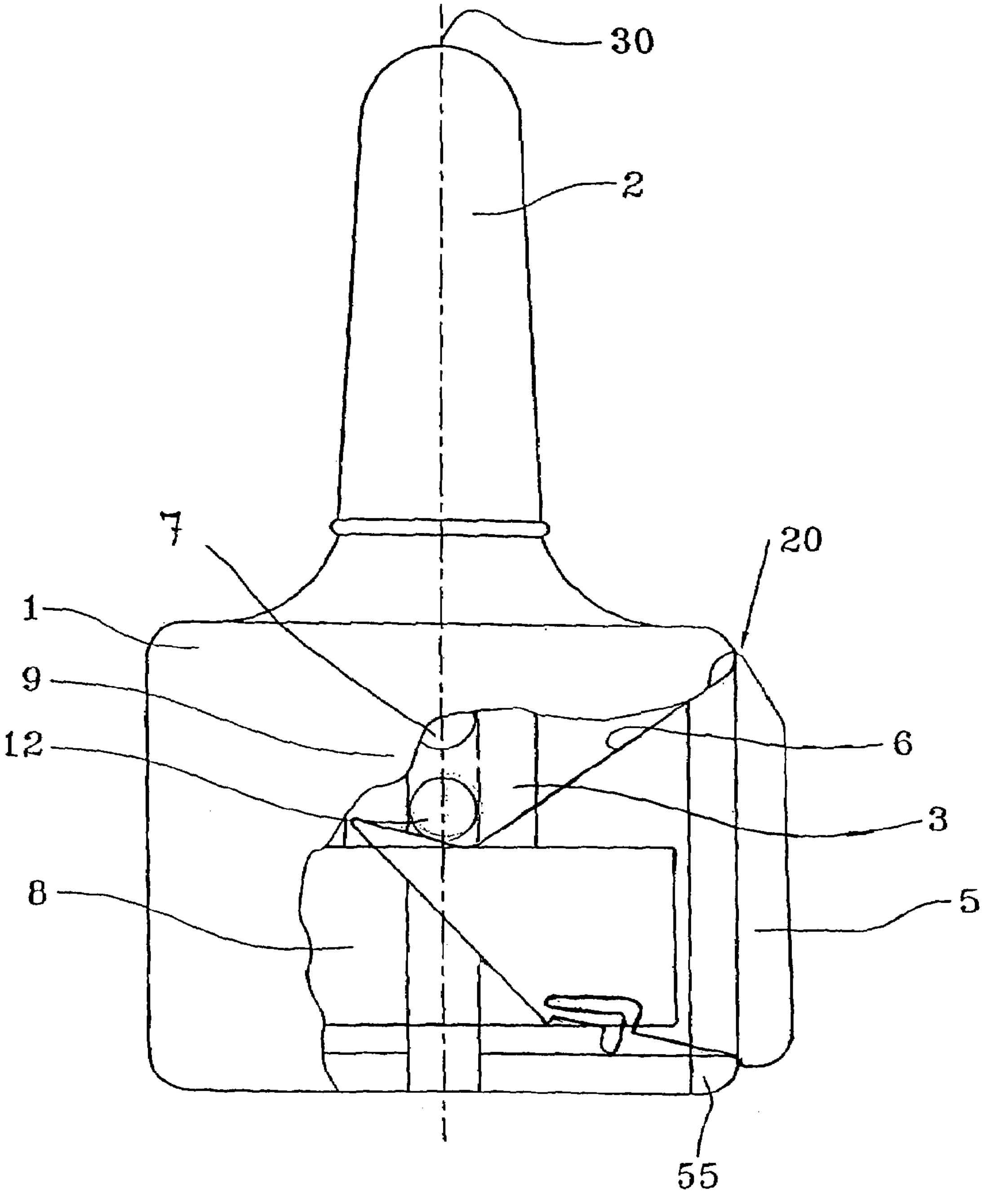
FIG. 4 is a view of the fluid dispenser in an actuating position for a second half dose.

With reference to the FIGS. 1-4, the fluid dispenser device shown comprises a body 1 in which a fluid reservoir 3 is provided that contains two half-doses of fluid. A dispensing orifice 30 is provided for dispensing said two half-doses of fluid. Advantageously, the dispensing orifice 30 is part of a nasal dispensing head 2, so that the two half-doses are dispensed into respective ones of the nostrils of the user. A dispensing member, such as a piston 8 is mounted to slide inside the reservoir 3, said dispensing member 8 being moved by an actuating element 5 on which the user exerts a force in order to move said dispensing member 8. Dose-splitting means 7, 12 are provided for splitting the dose of fluid contained in the reservoir into two half-doses, a first half-dose being dispensed the first time the device is actuated, and a second half-dose being dispensed the second time the device is actuated. Advantageously, as shown in the drawing, and as described in French Patent Application No. 00 11425, said dose-splitting means may be implemented in the form of projections or lugs, e.g. in pairs, a first pair of projections 7 co-operating with the actuating element 5 to dispense the first half-dose, and a second pair of projections 12 co-operating with the actuating element 5 to dispense the second half-dose. In particular, said second pair of projections 12 may be implemented in elastically deformable manner, so that said second pair of projections 12 moves out of the way while dispensing of the first half-dose is being actuated, thereby allowing said first pair of projections 7 to go past. Then, said second pair of projections 12 comes into place in the initial position originally occupied by the first pair of projections 7 ready for the dispenser to be actuated a second time to dispense the second half-dose. Advantageously, the actuating element 5 is returned to its rest position automatically between the two occasions on which the dispenser is actuated, so that the user merely has to press twice in succession on the actuating element 5 in order to dispense the two half-doses, without having to manipulate the device and without using the other hand. Naturally, other means for splitting the dose and other means for actuating the piston 8 may be imagined.

In the example shown in the figures, the actuating element 5 is a lateral actuating element which moves in a direction that is substantially transverse to the direction in which the piston 8 moves. More particularly, in the example shown in the figures, the actuating element 5 is mounted to pivot on the body 1 by means of a hinge 20, and it has a cam surface 6 which co-operates respectively with the first pair of projections 7 for dispensing the first half-dose, and with the second pair of projections 12 for dispensing the second half-dose.

Preferably, said first and second pairs of projections extend through a groove 9 provided for this purpose and which makes co-operation possible between the actuating means 5 and said pairs of projections.

In the invention, the device further comprises energy accumulation means which are adapted to accumulate energy in the hand of the user before enabling each half-dose to be dispensed. More precisely, the energy accumulated in the hand of the user is released suddenly from a predetermined force, said predetermined force exerted by the user on the actuating element 5 therefore overcoming said energy accumulation means and thus ensuring that each half-dose is dispensed in full by delivering sudden and quick thrust to the dispensing member 8.

With reference to the figures, an advantageous embodiment of the energy accumulation means is shown. In this embodiment, the energy accumulation means comprise an elastically deformable catch 50, at the end of which a lug 51 is advantageously provided, said catch 50 co-operating with a portion 55 of the body 1 so that said catch deforms only when it is subjected to the predetermined force exerted on the actuating element 5. Naturally, the energy accumulation means may be implemented differently, but it is preferable to avoid providing the energy accumulation means with breakable bridges of material.

The accumulation means of the present invention are designed to be disposed between two elements of the device that move relative to each other. Thus, in the example shown in the figures, the energy accumulation means are disposed between the actuating element 5 and the body 1. However, it is also possible to consider disposing them between the actuating element 5 and the dispensing member 8, e.g. at the cam surface 6, or else between the dispensing member 8 and the body 1 of the device. The energy accumulation means may be implemented differently, e.g. by means of bumps that can be overridden or elastically deformed by said predetermined force exerted on the actuating element 5.

Through its combination of characteristics consisting in providing a system that can be actuated laterally with one hand, and in providing means for accumulating energy in said hand that actuates the device, the present invention guarantees that each half-dose is dispensed reliably and in full in the respective nostril of the user, while making it impossible for the two half-doses to be dispensed accidentally in the same nostril, the device of the invention being simple to manufacture, to assemble, and to use, while guaranteeing total reliability.

The present invention is described with reference to a particular embodiment of it, but naturally the person skilled in the art may make any necessary modifications to it without going beyond the ambit of the present invention as defined by the accompanying claims.

The invention claimed is:

1. A nasal fluid spray device comprising a body (1), a fluid reservoir (3) containing two half-doses of fluid, each half-dose being for dispensing in a respective nostril, a dispensing orifice (30), and dispensing means (5, 6, 7, 8, 9) for dispensing a respective half-dose of fluid each time the dispensing means are actuated, said dispensing means being implemented so that each of the half-doses of fluid can be dispensed during a respective one of two successive occasions on which the dispensing means are actuated, it being possible to actuate the dispensing means on said successive occasions by the user of the device using a single hand, the nasal spray device further comprising energy accumulation means (50, 51, 55) adapted to accumulate energy in the hand of the user, said energy being released suddenly as of a predetermined force exerted by the hand of the user on said dispensing means, thereby guaranteeing that each of the half-doses is sprayed in full, said dispensing means comprising a dispensing member (8) mounted to slide in said reservoir (3) for dispensing the fluid, and dose-splitting means (7, 12) for dispensing a half-dose of fluid each time the dispensing means are actuated, said nasal spray device being characterized in that the dispensing means further comprise an actuating element (5) mounted to move between a rest position and an actuating position, and on which the user exerts an actuating force to move said dispensing member (8) inside said reservoir (3), said actuating element being mounted to move in a direction substantially transverse to the direction in which the dispensing member (8) moves.

2. A device according to claim 1, in which the dose-splitting means (7, 12) are secured to said dispensing member (8), and are formed by a first projection (7) co-operating with the actuating element (5) when the device is actuated for the first time to dispense the first half-dose of fluid, and a second projection (12) adapted to move out of the way while the first half-dose of fluid is being dispensed, said second pair of projections (12) co-operating with said actuating element (5) after the first half-dose has been dispensed, so as to dispense the second half-dose when the device is actuated for the second time.

3. A device according to claim 1, in which said dose-splitting means (7, 12) co-operate with said actuating element (5) to return it to its rest position after the first half-dose has been dispensed.

4. A device according to claim 1, in which said actuating element (5) has a cam surface (6) co-operating with said dispensing member (8), preferably via said dose-splitting means (7, 12).

5. A device according to claim 1, in which said energy accumulation means (50, 51, 55) are exempt from breakable bridges of material.

6. A device according to claim 5, in which said energy accumulation means (50, 51, 55) are provided between said actuating element (5) and said body (1) of the device.

7. A device according to claim 1, in which said energy accumulation means comprise an elastically deformable element (50) which deforms when it is subjected to said predetermined force.

8. A device according to claim 1, in which said energy accumulation means comprise an elastically deformable catch (50) provided on one of two elements (5, 1; 8, 1; 5, 8) that move relative to each other while the device is being actuated, said elastically deformable catch (50) co-operating with the other of said two elements that move relative to each other to prevent them from moving relative to each other until a predetermined force is applied that is adapted to deform said elastically deformable catch (50).

9. The device according to claim 1, wherein the dispensing member is a piston mounted to slide in the reservoir for dispensing the fluid.

* * * * *